(12) United States Patent
Arifin et al.

(10) Patent No.: US 8,895,275 B2
(45) Date of Patent: Nov. 25, 2014

(54) CONVERSION OF CELLULOSIC MATERIALS INTO GLUCOSE FOR USE IN BIOETHANOL PRODUCTION

(75) Inventors: Zainudin Bin Arifin, Kuala Lumpur (MY); Teow Chong Teoh, Kuala Lumpur (MY)

(73) Assignee: Universiti Malaya, Kuala Lumpur (MY)

( * ) Notice: Subject to any disclaimer, the term of this patent is extended or adjusted under 35 U.S.C. 154(b) by 0 days.

(21) Appl. No.: 13/146,207

(22) PCT Filed: Jan. 29, 2010

(86) PCT No.: PCT/MY2010/000018
§ 371 (c)(1),
(2), (4) Date: Jul. 26, 2011

(87) PCT Pub. No.: WO2010/104371
PCT Pub. Date: Sep. 16, 2010

(65) Prior Publication Data
US 2011/0281317 A1    Nov. 17, 2011

(30) Foreign Application Priority Data

Mar. 12, 2009  (MY) ................. PI 20091000

(51) Int. Cl.
| | | |
|---|---|---|
| *C12P 7/10* | (2006.01) | |
| *C12P 19/02* | (2006.01) | |
| *C13K 1/02* | (2006.01) | |
| *C12P 7/08* | (2006.01) | |

(52) U.S. Cl.
CPC . *C13K 1/02* (2013.01); *Y02E 50/16* (2013.01); *C12P 7/08* (2013.01)
USPC .......................................... 435/165; 435/105

(58) Field of Classification Search
None
See application file for complete search history.

(56) References Cited

U.S. PATENT DOCUMENTS

| | | |
|---|---|---|
| 4,529,699 A | 7/1985 | Gerez et al. |
| 5,597,714 A | 1/1997 | Farone et al. |
| 2004/0016525 A1 | 1/2004 | Gervais |
| 2008/0008783 A1 | 1/2008 | Dale |

FOREIGN PATENT DOCUMENTS

| | | |
|---|---|---|
| GB | 521884 | 6/1940 |
| WO | 2004081185 | 9/2004 |

OTHER PUBLICATIONS

S. Al-Asheh et al. Concentration of sucrose solutions via vacuum membrane distillation. Desalination. 2006. 195:60-68.*
CA Cardona et al. Fuel ethanol production: Process design trends and integration opportunities. Bioresource Technology. 2007. 98:2415-2457.*
De Lemos Esteves, F. et al. Improving the alkalophilic performances of the Xyl1 xylanase from *Streptomyces* sp. S38: Structural comparison and mutational analysis. 2005. Protein Science. 14:292-302.*
Smith GF. Wet Oxidation of Organic Matter Employing Perchloric Acid at Graded Oxidation Potentials and Controlled Temperatures. 1957. Analytica Chimica Acta. 17:175-185.*
Smith GF et al. A New General Procedure in the Low-Temperature Wet Oxidation of Organic Compositions. 1960. Talanta. vol. 4, pp. 185-193.*

* cited by examiner

*Primary Examiner* — David J Steadman
*Assistant Examiner* — Paul Holland
(74) *Attorney, Agent, or Firm* — Preston Smirman; Smirman IP Law, PLLC

(57) ABSTRACT

A method for producing an aqueous sugar solution from cellulosic materials comprising the steps of heating ground cellulosic materials with perchloric acid; neutralizing the heated materials with an alkali to yield a salt precipitate; and filtering the salt precipitate off to obtain the aqueous sugar solution.

6 Claims, No Drawings

CONVERSION OF CELLULOSIC MATERIALS INTO GLUCOSE FOR USE IN BIOETHANOL PRODUCTION

CROSS-REFERENCE TO RELATED APPLICATION

The instant application claims priority to PCT International Application No. PCT/MY2010/000018, filed on Jan. 29, 2010, pending, and Malaysian Patent Application No. PI 20091000, filed Mar. 12, 2009, pending, the entire specifications of both of which are expressly incorporated herein by reference.

FIELD OF INVENTION

The present invention relates to a method for producing sugar from cellulosic materials. In more particular, the present invention provides a method for saccharifying cellulosic materials to sugar using a chemical process, wherein the sugar produced is used in the synthesis of bioethanol.

BACKGROUND OF THE INVENTION

Bioethanol derived from cellulosic biomass is unarguably the best candidate to be used as an alternative fuel in the light of the dwindling global fossil fuel supplies. Many parts of the world produce huge amounts of cellulosic biomass, much of which have never been reused or recycled. These biomass often end up as waste material that are incinerated, land-filled or left to fallow. The thought that if every scrap of cellulose biomass is converted to bioethanol is mind staggering, as the mass conversion to bioethanol could significantly help meet the global transportation fuel needs.

The present production of bioethanol from cellulosic biomass faces the problem of hydrolyzing recalcitrant cellulosic biomass to sugar in a quick and cost-effective manner. The current method for deconstructing cell-wall biopolymers into sugar building blocks takes the form of chemical and biological methods. The chemical methods are generally energy-intensive and often require harsh conditions, while the biological methods are dependent on the discovery and invention of effective genome-based cellulase-producing microorganisms.

The conventional method of producing bioethanol starts with the hydrolysis of cellulosic biomass to form glucose as described by the Arkanol process. In this process, concentrated sulphuric acid of 70% to 77% strength is added to the biomass. This was followed by an initial heating to 50° C., then dilution, and the final mixture is further heated to 100° C. for one hour. A gel is produced from this process which is pressed to release an acid-sugar mixture and the acid is separated from the sugar using a chromatographic column. The method appears to require a high input of energy.

It is commonly known in the art that the use of concentrated sulphuric acid often leads to charring of the sugar solution because concentrated sulphuric acid is a strong dehydrating agent. As a result, other methods such as the use of dilute sulphuric acid have also been developed. The hemicellulose portion of the biomass is hydrolyzed using 0.5% sulphuric acid at 190° C. and the cellulose portion is hydrolyzed using 0.4% sulphuric acid at 215° C. The solution is then neutralized and recovered. Pressures of up to 15 atm are applied to help hydrolyze the cellulosic biomass. This process appears to suffer from the need to have a high input of energy.

The step of the neutralization of sulphuric acid is done by using calcium hydroxide, calcium oxide or other calcium bearing material to give calcium sulphate, $Ca_2SO_4.5H_2O$, or gypsum as a side product. This product is difficult to be separated out from the sugary solution. Besides, the large amount of calcium sulphate produced leads to disposal problems due to its limited usage.

There are a few patented technologies over the prior arts relating to the production process of cellulosic bioethanol. One of the patented technologies, U.S. Pat. No. 5,597,714, discloses a strong acid hydrolysis process of cellulosic and hemicellulosic materials. The acids used include phosphoric acid and sulfuric acid. Another U.S. Pat. No. 4,529,699 also relates to an acid hydrolysis of cellulosic materials using phosphoric acid, sulfuric acid, sulfurous acid or hydrochloric acid.

However, all these methods require high temperature and/or high pressure that are maintained over a long period. The process appears to be complicated, time-consuming and inconvenient, particularly in the process of extracting off the sugar produced.

The use of a superacid, dilute perchloric acid has also been disclosed in British Patent No. GB521884. This acid is used in the manufacture of cellulose ester, especially cellulose acetate from cellulosic material. Nevertheless, there is no technical guidance if the cellulose acetate can be converted to fermentable or simple sugar for bioethanol production.

U.S. Patent Publication No. 20080008783 disclosed uses alkali instead of acid to produce monosaccharides. The alkali used is concentrated ammonium hydroxide with or without anhydrous ammonia addition. Treatment of cellulosic material using base can destroy the lignin and hemicellulose which helps in saccharification. Apart from the complicated equipment set-up including pump, reactor, condenser and others, this process also requires high temperature and energy input.

There is also another process for treating lignocellulosic material as disclosed in U.S. Patent Publication No. 20040016525 that relates to the use of a condition in which the pH shall not be less than 8. After exposing the cellulosic material to this pH condition and steaming it at a first pressure, it is then discharged explosively to a second pressure before it can be used in the synthesis of bioethanol. Likewise, the process appears to be complicated, inconvenient, time- and energy-consuming.

The biological method focuses on the use of plants and microbes for the use of bioethanol production, such as the *Trichoderma reesei* (the cotton rot fungus) or *Populus trichocarpa* (a poplar). The attempts to deconstruct the cell-walls of biopolymers into sugar building blocks are presently beset with the high cost of enzymes, the quick denaturation of enzymes leading to slow conversion and the public's fear of genetically-engineered microorganisms that could be inadvertently released to the environment. Even the approach to hydrolysis of cellulosic materials using the combination of chemical and biological means faces over-riding factors such as costs and efficiency.

Therefore, it is desirable for the present invention to provide a method for producing sugar from cellulosic material which is more simple yet innovative to overcome some of the drawbacks of the prior arts.

SUMMARY OF INVENTION

The primary object of the present invention is to provide a method for producing sugar from cellulosic materials which uses a suitable partially concentrated acid and applies an innovative concept in the extraction of the sugar solution for further use.

Another object of the present invention is to provide a method for producing sugar from cellulosic material which is simpler, more convenient, more effective, less energy- and time-consuming.

Still another object of the present invention is to optimize the use of cellulosic biomass derived from various sources as a useful raw material in the production of bioethanol.

Yet another object of the present invention is to provide a method for recycling waste material, thus offering an alternative source of fuel which is renewable, biodegradable and environmentally friendly.

At least one of the preceding objects is met, in whole or in part, by the present invention, in which one of the embodiments of the present invention describes a method for producing an aqueous sugar solution from cellulosic materials comprising the steps of heating ground cellulosic materials with perchloric acid; neutralizing the heated materials with an alkali to yield a salt precipitate; and filtering the salt precipitate off to obtain the aqueous sugar solution. Preferably, the perchloric acid used is partially concentrated with 60% to 72% in concentration.

In one of the preferred embodiments of the present invention, the heating step is conducted at a temperature range of 30° C. to 70° C. It can also be conducted at room temperature, however the reaction is slower at lower temperatures.

Another preferred embodiment of the present invention discloses that the cellulosic materials are derived from paper, paddy straw, wood chip, leaves, saw dust, mushroom waste, fruit skins, weeds, cotton, plywood, grass, pressed oil-palm fibres, baggasse, corn stovers or a combination of any two or more thereof.

Preferably, the alkali is potassium hydroxide, rubidium hydroxide, caesium hydroxide, calcium hydroxide, calcium oxide or calcium bearing material. Most preferably, the alkali used is potassium hydroxide.

Still another preferred embodiment of the present invention is a method for producing an aqueous sugar solution from cellulosic materials which further comprises a step of concentrating the aqueous sugar solution. Preferably, the aqueous sugar solution is concentrated by vacuum stripping. It can also be done by simple evaporation using heat from the sun or other sources.

Further embodiment of the present invention is an aqueous sugar solution produced by any of the methods set forth in the preferred embodiments.

The present invention also discloses a method for synthesizing bioethanol by fermenting the aqueous sugar solution with yeast and distilling out the bioethanol; wherein the aqueous sugar solution is produced from cellulosic materials according to any of the methods set forth in the preferred embodiments.

One skilled in the art will readily appreciate that the present invention is well adapted to carry out the objects and obtain the ends and advantages mentioned, as well as those inherent therein. The embodiments described herein are not intended as limitations on the scope of the invention.

DETAILED DESCRIPTION OF THE INVENTION

The present invention relates to a method for producing sugar from cellulosic materials. In more particular, the present invention provides a method for saccharifying cellulosic materials to sugar using a chemical process, wherein the sugar produced is used in the synthesis of bioethanol.

Hereinafter, the invention shall be described according to the preferred embodiments of the present invention and by referring to the accompanying description. However, it is to be understood that limiting the description to the preferred embodiments of the invention is merely to facilitate discussion of the present invention and it is envisioned that those skilled in the art may devise various modifications without departing from the scope of the appended claim.

The present invention discloses a method for producing an aqueous sugar solution from cellulosic materials comprising the steps of heating ground cellulosic materials with perchloric acid; neutralizing the heated materials with an alkali to yield a salt precipitate; and filtering the salt precipitate off to obtain the aqueous sugar solution.

The saccharification process of the cellulosic materials to sugar embodied herein can be conducted at room temperature, with no restriction to a temperature which is lower or higher.

In the present invention, the cellulosic materials are preferably derived from paper, paddy straw, wood chip, leaves, saw dust, mushroom waste, fruit skins, weeds, cotton, plywood, grass, pressed oil-palm fibres, baggasse, corn stovers or a combination of any two or more thereof. These cellulosic materials are preferably cellulosic biomass obtained from recycled or waste biological sources. However, the present invention does not intend to limit the use of other cellulosic materials available. Preferably, the cellulosic biomass is pretreated according to conditions and then ground into a desired range of particle size prior to use. According to the preferred embodiment of the present invention, the desired particle size of the cellulosic materials after grinding is up to 1 mm, as larger sizes will cause delayed dissolution and slight charring.

In the present invention, partially concentrated perchloric acid having a concentration of 60% to 72% is the most suitably applied superacid for the saccharification of cellulosic materials to sugars. Similar chemicals such as perbromic and periodic acids are not suitable because perbromic acid is not stable giving bromine and oxygen gases spontaneously and periodic acid is a solid. Moreover, they are not common acids.

According to the preferred embodiment of the present invention, a partially concentrated perchloric acid (60% to 72%) is used. Preferably, the partially concentrated perchloric acid which is commercially produced at 60% to 62% (~3.5 $H_2O$) or 70% to 72% (~2.0 $H_2O$) is added into the cellulosic materials in a weight ratio of approximately 4~5:1 (perchloric acid: cellulose). Optionally, it can be measured in a volume to weight ratio of 5:2. For instance, 83.5 g or 50 ml of partially concentrated perchloric acid can be added into 20 g of cellulosic materials. It is to be noted that the use perchloric acid solutions of a higher concentration should be avoided as they are unstable and could violently decompose. As it is an extremely powerful oxidizing agent, the perchloric acid solution having unwanted impurities or pure or anhydrous form can react explosively with most organic materials. In addition, the anhydrous or pure perchloric acid is sensitive to shock and could explode. It is safer to use partially concentrated perchloric acid as they show moderate properties within the temperatures as embodied herein which is more appropriate for the reaction disclosed in the present invention. The cellulosic materials will be heated, dissolved and hydrolyzed.

In one of the preferred embodiments of the present invention, the heating step is conducted at a temperature range of 30° C. to 70° C. It can also be conducted at room temperature, however the reaction is slower at lower temperatures. The heating process is essential to achieve complete saccharification. The mixture of cellulosic materials and the partially concentrated perchloric acid will become homogeneous and a thick clear caramel sugar solution will be formed. It is to be noted that this mixture shall not be heated for more than 5 minutes so as to avoid caramelization or charring of sugars.

Subsequently, an equal volume ratio of distilled water to partially concentrated perchloric acid, for example 50 ml of distilled water to 50 ml of perchloric acid, is added to obtain a clear pale golden-coloured solution and the container is chilled in ice for neutralization.

Subsequently, an alkali is added into the mixture to neutralize its acidity. The alkali is preferably potassium hydroxide, rubidium hydroxide or caesium hydroxide, calcium hydroxide, calcium oxide or calcium bearing material. According to the most preferred embodiment of the present invention, the alkali applied is potassium hydroxide. Most preferably, solid potassium hydroxide is added into the mixture in a weight ratio of 3.5:5.0~8.5 (potassium hydroxide: perchloric acid) to neutralize 80% of the acidity and the remaining 20% is preferably neutralized by 10 M potassium hydroxide to expedite the process. However, the 10 M potassium hydroxide solution can also be applied alone but this will result in a slower neutralization process. The desired pH to be obtained is approximately 6.8 to 7.0. A suitable amount of water can also be added to ease the mixing and reading of pH value. In accordance with the preferred embodiment, the neutralization process is conducted in ice to avoid excessive build-up of heat. A white salt precipitate, which is potassium perchlorate, will be formed after the neutralization of potassium hydroxide.

The present invention can further comprise a step of concentrating the aqueous sugar solution, preferably by vacuum stripping or simple evaporation. The potassium perchlorate salt can be isolated by filtration and the pale golden-coloured aqueous solution is subjected to rotary evaporation in vacuum at a temperature range of approximately 70° C. to 80° C. The golden-coloured filtrate obtained still contains approximately 1.5% of potassium perchlorate salt, as this is the reported solubility of potassium perchlorate at room temperature. More potassium perchlorate salt can be salted-out when the aqueous sugar solution becomes more concentrated. The concentrated aqueous sugar solution can be filtered a few times again and chilled overnight to obtain the maximum amount of precipitate. The pH may be lowered by 0.5 after the concentration process. Thus, it can be re-neutralized with dilute potassium hydroxide and re-filtered after chilling to eliminate the remaining amount of potassium perchlorate precipitate in order to acquire a purer sugar solution.

The eliminated potassium perchlorate is a strong oxidizing agent and can be dangerously explosive if improperly handled. Its presence in the sugar solution must be eliminated or reduced as much as possible. However, it is a useful material to be used in the manufacture of matches or incendiaries.

One of the advantages of the present invention is, the present invention allows the recycling of perchloric acid. It can be recycled by treating the perchlorate salt with dilute sulphuric acid to yield potassium sulfate and perchloric acid. The potassium sulphate can then be precipitated from the solution and filtered off. The potassium sulfate salt precipitate could be used as a fertilizer; whereas the filtrate, perchloric acid, could be re-used for the hydrolysis of cellulosic materials as set forth in the foregoing description. One of the advantages of the present invention is that the present invention allows the recycling of perchloric acid. It can be recycled by treating the potassium perchlorate salt with dilute sulphuric acid to yield potassium sulfate and perchloric acid. The potassium sulphate can then be precipitated from the solution and filtered off. The potassium sulfate salt precipitate could be used as a valuable fertilizer; whereas the filtrate, perchloric acid, could be re-used for the hydrolysis of cellulosic materials as set forth in the foregoing description.

Further embodiment of the present invention is an aqueous sugar solution produced by any of the methods set forth in the preferred embodiments. The saccharified product is a golden-coloured sugar solution, which is mainly made up of reducing sugars. The aqueous sugar solution tastes sweet and is capable of giving a positive Benedict's test. The sugar solution is suitable to be used for the fermentation process.

The present invention also discloses a method for synthesizing bioethanol by fermenting the aqueous sugar solution with yeast and distilling out the bioethanol; wherein the aqueous sugar solution is produced from cellulosic materials according to any of the methods set forth in the preferred embodiments.

Accordingly, the suitable yeast used in the present invention is the commonly available Baker's yeast derived from *Saccharomyces cerevisiae*. A person skilled in the art shall appreciate the fact that other suitable strains of yeast can also be used in the present invention. Preferably, 0.5 to 1.5% by weight of the Baker's yeast is added into the sugar solution. The sugar solution is left to ferment and the ethanol can be distilled out after the fermentation is complete. It is to be aware that particular care has to be taken during the heating process to avoid heating to dryness of ethanolic substrate solution. The distillation flask can be topped-up with more fermented liquid when the liquid level reaches a quarter-full.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to without departing from the scope of the invention.

EXAMPLE

The invention can be further described with reference to the following examples. These examples are provided to illustrate different aspects and embodiments of the present invention and are not intended in any way to limit the disclosed invention, which is limited only by the claims.

Example 1

Scarification of Pure Cellulose 20 g of pure cellulose from Sigma was dissolved in 50 ml of 70% perchloric acid. The homogeneous mixture was heated at 60° C. for approximately 5 minutes to obtain a clear solution. An equal volume of water was added to ease neutralization later. The dilute mixture was chilled in ice and neutralized with 35 g of potassium hydroxide (KOH) pellets with stirring to obtain a pH of around 1.3. Approximately 10 ml of 10 M KOH was added to obtain a pH of around 6.8 to 7.0. The slurry formed was filtered and the filtrate was evaporated under vacuum to obtain a golden-coloured syrup and filtered again. The golden-coloured syrup was chilled overnight and filtered again. This final syrup can be used to feed the Baker's yeast for ethanol production.

Example 2

Saccharification of Office-Used A4 Paper

Office-used A4 papers were soaked with 1 M KOH overnight and washed with water to get rid of any stains. The wood fibres formed were further reacted with dilute hydrochloric acid (HCl) to get rid of chalk that is used as a filler in A4 papers. The salt produced from chalk was washed with water and the pure cellulose obtained was then dried in the oven overnight. 20 g of the pure cellulose was ground into powder of up to 1 mm in size and was dissolved in 50 ml of 70% perchloric acid. The homogeneous mixture was heated at 60° C. for about 5 minutes to obtain a clear solution. An equal volume of water was added to ease neutralization. The dilute mixture was chilled in ice and neutralized with 35 g of KOH pellets with stirring to obtain a pH of around 1.3. Around 10 ml of 10 M KOH was added to obtain a pH of around 6.8 to 7.0. The slurry formed was filtered and the filtrate was evaporated under vacuum to obtain a golden-coloured syrup and filtered again. The golden-coloured syrup was chilled overnight and filtered again. This final syrup can be used to feed the Baker's yeast for ethanol production.

Example 3

Saccharification of Paddy Straw

Paddy straw was de-lignified by soaking it overnight with 1 M KOH. The cellulose was washed with water, to get rid of the KOH and lignin, and dried in the oven overnight. The cellulose obtained was ground into powder of up to 1 mm in size and was dissolved in 50 ml of 65% to 70% perchloric acid. The homogenous mixture was heated at 60° C. for about 5 minutes to obtain a clear solution. An equal volume of water was added to ease neutralization. The dilute mixture was chilled in ice and neutralized with 35 g of KOH pellets with stirring to obtain a pH of around 1.3. Around 10 ml of 10 M KOH was added to obtain a pH of around 6.8 to 7.0. The slurry formed was filtered and the filtrate was evaporated under vacuum to obtain a golden-coloured syrup and filtered again. The golden-coloured syrup was chilled overnight and filtered again. This final syrup can be used to feed the Baker's yeast for ethanol production.

The invention claimed is:

1. A method for producing an aqueous sugar solution from cellulosic materials, comprising:
    mixing ground cellulosic materials with a superacid to form a mixture, wherein the superacid is free of periodic acid, wherein the superacid is partially concentrated perchloric acid, wherein the perchloric acid is present in a concentration of 60% to 72%;
    heating the mixture for not more than 5 minutes, wherein the heating is conducted at a temperature range of 60° C. to 70° C.;
    chilling the heated mixture in ice to produce a chilled mixture;
    neutralizing the chilled mixture with an alkali to yield a salt precipitate wherein the alkali is selected from the group consisting of potassium hydroxide, rubidium hydroxide, caesium hydroxide, calcium hydroxide, calcium oxide, and combinations thereof;
    filtering the salt precipitate off to obtain the aqueous sugar solution; and
    treating the salt precipitate with sulfuric acid to yield a sulfate salt and perchloric acid, wherein the sulfate salt is selected from the group consisting of potassium sulfate, rubidium sulfate, caesium sulfate, and calcium sulfate.

2. The method of claim 1, wherein the cellulosic materials are selected from the group consisting of paper, paddy straw, wood chip, leaves, saw dust, mushroom waste, fruit skins, weeds, cotton, plywood, grass, pressed oil-palm fibres, bagasse, corn stovers, and combinations thereof.

3. The method of claim 1, wherein the weight ratio between the perchloric acid and the cellulosic materials is 4-5:1.

4. The method of claim 1, further comprising a step of concentrating the aqueous sugar solution.

5. The method of claim 4, wherein the aqueous sugar solution is concentrated by vacuum stripping.

6. A method for synthesizing bioethanol, comprising:
    mixing ground cellulosic materials with a superacid, wherein the superacid is free of periodic acid, wherein the superacid is partially concentrated perchloric acid, wherein the perchloric acid is present in a concentration of 60% to 72%;
    heating the mixture for not more than 5 minutes, wherein the heating is conducted at a temperature range of 60° C. to 70° C.;
    chilling the heated mixture in ice to produce a chilled mixture;
    neutralizing the chilled mixture with an alkali to yield a salt precipitate wherein the alkali is selected from the group consisting of potassium hydroxide, rubidium hydroxide, caesium hydroxide, calcium hydroxide, calcium oxide, and combinations thereof;
    filtering the salt precipitate off to obtain an aqueous sugar solution;
    fermenting the aqueous sugar solution with yeast to produce bioethanol;
    distilling out the bioethanol; and
    treating the salt precipitate with sulfuric acid to yield a sulfate salt and perchloric acid, wherein the sulfate salt is selected from the group consisting of potassium sulfate, rubidium sulfate, caesium sulfate, and calcium sulfate.

* * * * *